United States Patent [19]

Roman et al.

[11] 4,022,775

[45] May 10, 1977

[54] 3-OXOMETHYL-2-(1-NITRO-2-OXOETHYLIDENE)-TETRAHYDRO-2H-1,3-THIAZINES

[75] Inventors: Steven A. Roman, Oakdale, Calif.; James E. Powell, Rodmersham Green near Sittingbourne, England

[73] Assignee: Shell Oil Company, Houston, Tex.

[22] Filed: Mar. 3, 1976

[21] Appl. No.: 663,317

Related U.S. Application Data

[63] Continuation-in-part of Ser. No. 564,258, April 2, 1975, abandoned.

[52] U.S. Cl. .............................. 260/243 R; 424/246
[51] Int. Cl.$^2$ ...................................... C07D 279/06
[58] Field of Search ................................ 260/243 R

[56] References Cited

OTHER PUBLICATIONS

Hirai et al., "Syntheses and Reactions of 2-Substituted Thiazolidines" *Chem. Pharm. Bull.*, vol. 20, pp. 97–101 (1972).

*Primary Examiner*—John M. Ford

[57] ABSTRACT

Novel compounds defined in the title, useful as insecticides.

1 Claim, No Drawings

3-OXOMETHYL-2-(1-NITRO-2-OXOE-THYLIDENE)-TETRAHYDRO-2H-1,3-THIAZINES

This application is a continuation-in-part of copending application Ser. No. 564,258, filed Apr. 2, 1975, now abandoned.

DESCRIPTION OF THE INVENTION

It has been found that useful insecticidal activity is possessed by certain derivatives of tetrahydro-2H-1,3-thiazines substituted at the 3-position (i.e., on the ring nitrogen atom) by an oxomethyl moiety, and at the 2-position by a 1-nitro-2-oxoethylidene moiety, these derivatives being described by the formula:

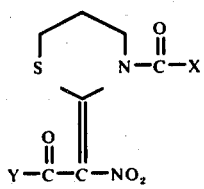

(I)

wherein X and Y each is R, R—O— or R—S—, R containing up to 30 carbon atoms and being alkyl, alkenyl, alkynyl, cycloalkyl, cycloalkylalkyl, haloalkyl, haloalkenyl, mono- and poly(alkoxy)alkyl, alkylthioalkyl, alkylsulfinylalkyl, alkylsulfonylalkyl: phenyl or phenalkyl, or any of these substituted on the ring by one to two of one or more of halogen, nitro, cyano, alkyl, aryl, alkoxy or phenoxy; is aminoalkyl, —CH$_2$—$_m$NR$^1$R$^2$, wherein $m$ is one or two, R$^1$ and R$^2$ is alkyl, alkenyl, cycloalkyl, phenyl or phenalkyl; or is —CH$_2$—$_n$R$^5$, wherein $n$ is zero, one or two, and R$^5$ is heterocyclic moiety selected from furanyl, tetrahydrofuranyl, dioxolanyl, thienyl, thiopyranyl, pyridinyl, pyrrolidinyl, morpholinyl and their -methyl and -ethyl counterparts.

When aliphatic, the moiety represented by R may be of straight-chain or branched-chain configuration and preferably contains no more than 10 carbon atoms. The preferred aminoalkyl moieties are dialkylaminomethyl and -ethyl. The preferred phenyl moieties are optionally substituted-phenyl.

Because of their insecticidal activity characteristics, a preferred sub-class of the genus of the invention consists of these compounds wherein Y is lower alkyl, or lower alkoxy, straight-chain, branched-chain or cyclic in configuration, and containing, for example, from 1 to 6 carbon atoms.

For illustration, preparation of typical species esters of the genus is described in the examples included hereinafter. other typical, illustrative species of this genus include those wherein the symbols represent the following moieties, this manner of naming these species being accurate, yet pointing out the differences between the different species more clearly than if the entire, complicated name of each species were to be given:

| X | Y |
|---|---|
| ethoxy | benzyloxy |
| ethoxy | benzyl |
| methoxy | phenoxy |
| ethoxy | phenyl |
| methoxy | methylthio |
| methylthio | methylthio |
| ethyl | benzyl |
| ethyl | benzyloxy |
| 2-(methylthio)ethoxy | methyl |
| 2-(methylthio)ethoxy | 2-(methylthio)ethoxy |

-continued

| X | Y |
|---|---|
| 2-furanyl | methyl |
| methyl | 2-thienylmethyl |
| 2-(4-morpholinyl)ethyl | methoxy |
| 3-pyridylmethyl | methoxy |
| methyl | 2-pyridyl |
| tetrahydro-2H-thiopyran-3-yl | methyl |
| phenyl | vinyl |
| 2-propynyl | methoxy |
| methyl | cyclohexyloxy |
| cyclopropyl | methoxy |
| 2,2-dimethyl-1,3-dioxolan-4-ylmethoxy | ethyl |
| 2-(phenylthio)ethyl | methoxy |
| ethoxy | 2-(phenylthio)ethyl |
| methyl | phenoxy |
| methoxy | phenoxy |
| dimethylaminomethyl | methoxy |
| methyl | m-dichlorobenzyloxy |
| phenyl | (dimethylamino)methyl |

Compounds of this invention can be prepared by four general procedures, all involving treatment of an alkali metal (e.g., sodium) derivative of an appropriate thiazine precursor with the appropriate acid chloride, chloroformate or chlorothioformate, the four types of compounds involved being as follows:

A. X and Y both are RO— or RS—;
B. X is R and Y is RO— or RS—;
C. X and Y both are R;
D. X is RO— or RS— and Y is R.

The appropriate thiazine precursors are represented by the formulae:

1. For preparation of types A and B:

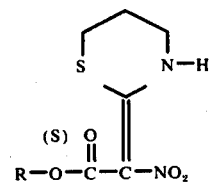

(II)

2. For preparation of types C and D:

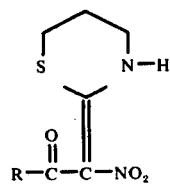

(III)

Compounds of formula II are the subject of application Ser. No. 554,371, now U.S. Pat. No. 3,962,234, while compounds of formula III are the subject of application Ser. No. 547,417, now U.S. Pat. No. 3,962,225. For the purpose of describing the preparation of these precursors, the pertinent portions of said applications are incorporated herein.

The acid chloride, chloroformate and chlorothioformate reactants are in many cases known compounds, and in those cases when they are specifically novel, can be prepared by the procedures known in the art for the known analogs thereof.

The thiazine precursors are converted to the needed alkali metal derivatives by treatment with an alkali metal hydride, such as sodium hydride, preferably in a suitable liquid reaction medium, such as tetrahydrofuran, at a low temperature, for example, about 0° C. To enable efficient control of the often exothermic reaction, it may be found desirable to add slowly a solution or suspension of the thiazine to a stirred, cooled solution or suspension of the base, the mixture being stirred further until hydrogen ceases to evolve. The mixture then may be allowed to warm, for example to room temperature, to ensure completion of the reaction.

Treatment of the alkali metal derivative with the carbonylic reactant can be effectively carried out under similar conditions: adding a suspension or solution of the carbonylic reactant slowly to a stirred solution or suspension of the alkali metal derivative, the reaction mixture being cooled as necessary to maintain it at a low temperature — again, suitably about 0° C — then allowing the stirred mixture to warm, for example to room temperature, and stirring the warmed mixture for a period of time to ensure complete reaction.

It often will be found convenient to employ the same liquid reaction medium in both steps of the process, with tetrahydrofuran generally being quite suitable for this purpose. In such a case, the solution or suspension of the alkali metal derivative obtained as the product of the alkali metal hydride/thiazine reaction is treated directly with the solution or suspension of the carbonylic reactant.

The desired product can be isolated from the crude reaction mixture and purified by conventional methods, such as filtration, extraction, crystallization and elution (chromatography).

Preparation of compounds of type A also can be effected by treating a precursor of formula II with the appropriate acid anhydride, in a suitable solvent, such as methylene chloride or other haloalkane, using reaction conditions and product recovery and purification techniques described above.

These procedures for preparing compounds of this invention are illustrated in the following examples of the preparation of particular species of such compounds. In all cases the identity of the thiazine precursor had been established and the identity of the final product was confirmed, by elemental analysis and by infrared and nuclear magnetic resonance spectrum analyses:

EXAMPLE 1

1-(3-acetyltetrahydro-2H-1,3-thiazin-2-ylidene)-1-nitro-2-propanone (1)

A solution of 20.2 g of 1-nitro-1-(tetrahydro-2H-1,3-thiazine-2-ylidene)-2-propanone (1A; Example 2, Ser. No. 547,417, now U.S. Pat. No. 3,962,225) in 200 ml of tetrahydrofuran (THF) was added dropwise to a stirred suspension of sodium hydride (4.65 g of 57% dispersion in mineral oil in 100 ml of THF), the mixture being maintained at about 0°. After the addition was complete, stirring at 0° was continued until hydrogen evolution ceased. The stirred mixture then was allowed to warm to room temperature and stirred overnight. The mixture then was cooled to 0° and a solution of 8.2 g of acetyl chloride in 50 ml of THF was added dropwise. The mixture was stirred at 0° C for 30 minutes and then allowed to warm to room temperature gradually and stirred at room temperature for 90 hours. The reaction mixture then was poured into a mixture of chloroform and saturated sodium bicarbonate solution. The organic phase was separated, washed with water, saturated sodium chloride solution, dried (sodium sulfate) and stripped of solvent under reduced pressure to leave a dark viscous oil. The oil was dissolved in ethyl acetate, the solution was chilled and an equivalent amount of ether was added. The liquid phase was separated and stripped of solvent under reduced pressure. the resulting oil was dissolved in methylene chloride and extracted with 10% sodium hydroxide solution. The organic phase was separated, washed with water and saturated sodium chloride solution, dried ($Na_2SO_4$) and stripped of solvent under reduced pressure. The resulting liquid was triturated with ether and chilled to give 1, as a yellow solid, m.p.: 73.5°–76°.

EXAMPLE 2

Ethyl 5,6-dihydro-2-(1-nitro-2-oxopropyl-idene)-2H-1,3-thiazine-3(4H)-carboxylate (2)

A solution of 10.1 g of 1A in 100 ml of THF was added dropwise, at 0° C, to a suspension of 2.33 g of sodium hydride in 50 ml of THF. The stirred reaction mixture then was allowed to warm to room teperature and stirred for 75 hours. The mixture then was cooled to 0° and 6.3 g of ethyl chloroformate in 50 ml of THF was added dropwise. The stirred mixture then was allowed to warm to room temperature and stirred for 3 hours. The mixture then was taken up in 300 ml of water and extracted thrice with methylene chloride. The extracts were combined, washed with saturated sodium chloride solution, dried ($Na_2SO_4$) and the solvent evaporated under reduced pressure to leave an oil, which solidified when chilled. The solid was crushed under petroleum ether and collected to give 2, as a bright yellow solid, m.p. 52°–54°.

EXAMPLE 3

Methyl 5,6-dihydro-2-(2-methoxy-1-nitro-2-oxoethylidene)-2H-1,3-thiazine-3(4H)-carboxylate (3)

At 0° a solution of 16.0 g of methyl chloroformate in THF was added dropwise to a solution of the sodium derivative of 32.7 g of methyl nitro(tetrahydro-2H-1,3-thiazin-2-ylidene)acetate (3A; Example 2, Ser. No. 554,371) in THF. The stirred solution was then allowed to warm to room temperature and stirred overnight. The solvent was evaporated under reduced pressure and the residue was poured into ether. The ether phase was washed with water, dried ($MgSO_4$) and the solvent evaporated under reduced pressure. The resulting oil was mixed with pentane to give 3, as yellow crystals, m.p.: 71°–2°.

EXAMPLE 4

Methyl (3-acetyltetrahydro-2H-1,3-thiazin-2-ylidene)nitroacetate (4)

By the procedure described in Example 3, the sodium derivative of 32.7 g of 3A was treated with 13.4 g of acetyl chloride to give 4, as a yellow oil, boiling point not determined.

EXAMPLE 5

Methyl (3-(dichloroacetyl)-tetrahydro-2H-1,3-thiazin-2-ylidene)nitroacetate (5)

4.4 g of 3A was added in portions to a stirred solution of 10.0 g of dichloroacetic anhydride in 10 ml of methylene chloride at about 0°. The mixture was allowed to warm to room temperature and stirred overnight. The resulting mixture was diluted with methylene chloride, washed with saturated sodium bicarbonate solution, and with water, dried and stripped of solvent under reduced pressure. The residue was taken up in methylene chloride, the solution filtered through Florisil and the solvent was evaporated under reduced pressure to give 5, as a bright yellow solid, m.p.: 121.5°–122.5°.

EXAMPLES 6–30

By procedures analogous to those described in Examples 1–4, the following additional individual species of compounds of formula I were prepared, each compound being described in terms of (a) example number, (b) compound number, (c) definitions of the moieties defied by X and Y and (d) physical description.

6; 6; cyclopropyl; methoxy; yellow solid; m.p.: 65°–66°.

7; 7; phenyl; methoxy; yellow solid; m.p.: 126.5°–127.5°.

8; 8; propyl; methoxy; yellow liquid; b.p.: not determined.

9; 9; vinyl; methoxy; yellow solid; m.p.: 55°–56°.

10; 10; benzyloxy; methoxy; yellow liquid; b.p.: not determined.

11; 11; phenyl; cyclopropylmethoxy; yellow solid; m.p.: 120°–121°.

12; 12; methylthio; methoxy; yellow solid; m.p.: 59°–60°.

13; 13; 4-methylphenyl; methoxy; yellow solid; m.p.: 137°–137.5°.

14; 14; 4-cyanophenyl; methoxy; pale yellow solid; m.p.: 142.5°–143°.

15; 15; 2,2-dimethyl-3,3-dichlorocyclopropyl; methoxy; yellow solid; m.p.: 88°–89°.

16; 16; allyloxy; methoxy; yellow solid; m.p.: 37.5°–38°.

17; 17; neopentyl; methoxy; yellow liquid; b.p.: not determined.

18; 18; methylthiomethyl; methoxy; yellow solid; m.p.: 80°–81.5°.

19; 19; 2-(methylthio)ethoxy; methoxy; yellow liquid; b.p.: not determined.

20; 20; methyl; propyl; amber liquid; b.p.: not determined.

21; 21; phenyl; propyl; yellow solid; m.p.: 78°–80.5°.

22; 22; phenyl; methyl; light brown solid; m.p.: 108°–110°.

23; 23; ethoxy; propyl; amber liquid; b.p.: not determined.

24; 24; ethyl; propyl; liquid; b.p.: not determined.

25; 25; methyl; phenyl; light yellow solid; m.p.: 105°–106°.

26; 26; pentyl; phenyl; yellow solid, m.p.: 96.5°–98°.

27; 27; phenyl; 2-(methylthio)ethyl; yellow solid, m.p.: not determined.

28; 28; p-cyanophenyl; phenyl; yellow solid; m.p.: 143°–144°.

29; 29; 4-cyanophenyl; propyl; amber oil, boiling point not determined;

30; 30; 1-ethylpropyl; phenyl; yellow solid; m.p.: 61°–63.5°.

As is disclosed in application Ser. No. 554,371, precursors of type B, also can be prepared by treating tetrahydro-(2-nitromethylene)-2H-1,3-thiazine with a 1-(R-oxycarbonyl)-3-methylimidazolium chloride by the method described by E. Guibe-Jampel, et. al., Bull. Soc. Chim. Fr. 1973 (3) (Pt. 2), pp. 1021–7. According to this method, the imidazolium chloride is prepared by treating 1-methylimidazole with the appropriate chloroformate, R—O—C(O)—Cl, preferably in a suitable solvent and at a low temperature, for example, about 0° C. A suitable general method for conducting this procedure comprises adding a solution of the chloroformate in tetrahydrofuran slowly (e.g., dropwise) to a cold (e.g., 0°) solution of the N-methylimidazole in the same solvent, stirring the cold mixture for a period of from about 15 minutes to 1 hour to ensure complete reaction, then adding to that stirred cold mixture a solution of the thiazine, then warming the stirred mixture to a temperature of from about room temperature to the reflux temperature, and stirring the warm mixture for a time to ensure complete reaction.

The desired product can be isolated from the crude reaction mixture and purified by conventional methods, such as filtration, extraction, crystallization and elution (chromatography). The use of this method for preparing such precursors is described in the following examples.

EXAMPLE 31 ethanethioic acid,
(3-benzoyltetrahydro-2H-1,3-thiazin-2-ylidene)nitro-,
S-ethyl ester (31)

To a mixture of 235 g of 5,6-dihydro-2-(methylthio)-4H-1,3-thiazine (A. F. McKay et al., J. Am. Chem. Soc., 80, 3339 (1950)) and 2 g of zinc chloride at approximately 115° in a nitrogen atmosphere, 263 g of ethyl nitroacetate (S. Zen et al., Kogyo Kagaku Zosshi, 74, 70 (1971)) was added dropwise over a 1.5 hour period. The mixture was held at 110°–120°. When evolution of methyl mercaptan ceased after 45 minutes further stirring of the heated mixture, 1 g of zinc chloride was added and the mixture was stirred at about 115° for 1.25 hours. An additional 1 g of zinc chloride then was added and stirring of the mixture at about 115° was continued for 1.5 hours. The mixture then was poured into a cooled 2/1 ether/isopropyl alcohol mixture. The crystallized product was collected, washed with ether and dried under reduced pressurre to leave a tan solid, m.p. 100°–102°, which on recrystallization from methanol gave ethyl nitro (tetrahydro-2H1,3-thiazin-2-ylidene)acetate as a pale yellow solid, m.p. 105°–106°.

2.3 g of 31A was added to 10 ml of 20% aqueous sodium hydroxide and the mixture was stirred at room temperature for 12 hours. The resulting solution was treated dropwise with 3.5 g of acetic acid. The addition was accompanied by vigorous gas evolution. The resulting mixture was extracted with methylene chloride and the extract was dried (magnesium sulfate) and concentrated under reduced pressure to give tetrahydro-2-(nitromethylene)-2H-1,3-thiazine (31B) as a pale yellow solid, m.p.: 76°–78°.

A solution of 13.7 g of ethyl chlorothiolformate in 50 ml of dry tetrahydrofuran was added to 9.0 g of 1-methylimidazole in 200 ml of dry tetrahydrofuran at 5°, over a 20-minute period. The mixture was stirred at 5° for 30 minutes, then 16.0 g of 31B was added all at once, and the stirred mixture was allowed to slowly warm to room temperature and was stirred overnight. The solvent was stripped, the residue dissolved in a mixture of water and methylene chloride. The two phases were separated, the water phase was extracted with methylene chloride, the methylene chloride solutions were combined, dried (MgSO$_4$), filtered and the solvent evaporated under reduced pressure, to leave an oil. The oil was stirred with a mixture of water and ether; solid material was filtered off and recrystallized from ethyl alcohol to give nitro(tetrahydro-2H-1,3-thiazin-2-ylidene ethanethioic acid, S-ethyl ester (31C) as a pale yellow solid, m.p.: 124°–124.5°.

2.2 g of 31C was added in portions over a ten-minute period to a stirred solution of 0.5 g of sodium hydride in 50 ml of tetrahydrofuran. To this stirred mixture then was added dropwise a solution of 1.6 g of benzoyl chloride in 10 ml of tetrahydrofuran. The resulting mixture was allowed to warm slowly to room temperature and was stirred for two hours. A few drops of water were added to decompose any remaining sodium hydride, then the mixture was diluted with chloroform and washed with water. The chloroform phase was separated, dried (MgSO$_4$) and the solvent stripped, to give an oil, which was washed with pentane and the residue crystallized from ether to give 31, as a yellow solid, m.p.: 114° (with decomposition).

EXAMPLE 32

In a similar manner was prepared the corresponding S-methyl ester (32), as a yellow solid, m.p.: 122°–123°.

Compounds of this invention exhibit useful insecticidal activity being of particular interest for control of the larvae "caterpillar" or "worm" forms of insects of the genus Heliothis, such as *H. Zea* (corn earworm, cotton bollworm, tomato fruitworm), *H. virescens* (tobacco budworm); the genus Agrotis, such as *A. ipsilon* (black cutworm); the genus Trichoplusia, such as *T. ni* (cabbage looper), and the genus Spodoptera, such as *S. littoralis* (Egyptian cotton leafworm). Some are also of interest for controlling aphids, whiteflies and houseflies. In tests that have been conducted they have exhibited low, or no, toxicity to other insects such as the 2-spotted spider mite and mosquito larva. Some act very rapidly providing "quick knock-down" of insects; in some cases even though the compound is not very toxic to the insects.

Activity of compounds of this invention with respect to insects was determined by using standardized tests to establish the LC$_{50}$ dosage (in milligrams of test compound per 100 milliliters of solvent or liquid carrier required in the solution or suspension of test compound used) that was required to kill 50% of the test insects. The test insects were the housefly, corn earworm, mosquito, pea aphid and 2-spotted spider mite.

All of compounds 1 through 31 were found to be inactive or but slightly active with respect to the mites and mosquito larvae. With respect to the corn earworm, all of the compounds were found to be active. With respect to the pea aphid, compounds 1, 2, and 20 were found to be active. With respect to the housefly, compounds 1–6, 8–12, 14–20, 22, 23, and 31 were found to be active.

In the course of these tests it was noted that compounds 1, 4, 5, 8, 9, 15, 18 and 20 acted very quickly on houseflies, compounds 1 and 20 acted very quickly upon pea aphids and compounds 1, 2, 4, 6–8, 12, 14, 20, 23 and 25 acted very quickly upon corn earworm.

The invention includes within its scope insecticidal compositions comprising an adjuvant — that is, a carrier optionally a surface-active agent — and, as active ingredient, at least one insecticide of this invention. Likewise the invention includes also a method of combatting insect pests at a locus which comprises applying to the locus an effective amount of at least one insecticide of the invention.

The term "carrier" as used herein means a material which may be inorganic or organic and of synthetic or natural origin with which the active compound is mixed or formulated to facilitate its application to the plant, seed, soil and other object to be treated, or its storage, transport or handling. The carrier may be a solid or a liquid.

Suitable solid carriers may be natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as for example, carbon and sulfur; natural and synthetic resins such as for example, coumarone resins, polyvinyl chloride and styrene polymers and copolymers, solid polychlorophenols; bitumen, waxes such as beeswax, paraffin wax and chlorinated mineral waxes; degradable organic solids such as ground corn cobs and walnut shells; and solid fertilizers, for example, superphosphates.

Suitable liquid carriers include solvents for the compounds of this invention and liquids in which the toxicant is insoluble or only slightly soluble.

Examples of such solvents and liquid carriers generally are water, alcohols, for example, isopropyl alcohol, ketones, such as acetone, methyl ethyl ketone, methyl isobutyl ketone and cyclohexanone; ethers; aromatic hydrocarbons, such as benzene, toluene and xylene; petroleum fractions, such as kerosene, light mineral oils, chlorinated hydrocarbons, such as carbon tetrachloride, perchlorethylene, trichloroethane, including liquefied normally vaporous gaseous compounds. Mixtures of different liquids are often suitable.

If used, the surface-active agent may be an emulsifying agent or a dispersing agent or a wetting agent. It may be nonionic or ionic. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; fatty acid salts of low molecular weight, mono-, di- and trialkylamines; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products; alkali or alkaline earth metal salts, preferably sodium salts, or sulfuric or sulfonic acids esters containing at least 10 carbon atoms in the molecule, for example, sodium lauryl sulfate, sodium secondary alkyl sulfates, sodium salts of sulfonated caster oil, and sodium alkyaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates or aerosols. Encapsulated formulations and controlled release formulations also are contemplated, as are bait formulations. Wettable powders are usually compounded to contain 25, 50 or 75%w of toxicant and usually contain, in addition to solid carrier, 3–10%w of stabilizer(s) and/or other additives such as penetrants or stickers. Dusts are usually formulated as a dust concentrate having a similar compositions to that of a wettable powder but without a dispersant, and are diluted in the field with further solid carrier to give a composition usually containing ½–10%w of toxicant. Granules may be manufactured by agglomeration or impregnation techniques. Generally, granules will contain ½–25%w toxicant and 0–10%w of additives such as stabilizers, slow release modifiers and binding agents. Emulsifiable concentrates usually contain, in addition to the solvent, and when necessary, co-solvent, 10–50%w/v toxicant, 2–20%w/v emulsifiers and 0–20%w/v of appropriate additives such as stabilizers, penetrants and corrosion inhibitors. Suspension concentrates are compounded so as to obtain a stable, non-sedimenting, flowable product and usually contain 10–75%w toxicant, 0–5% of dispersing agents, 0.1–10%w of suspending agents such as protective colloids and thixotropic agents, 0–10%w of appropriate additives such as defoamers, corrosion inhibitors, stabilizers, penetrants and stickers, and as carrier, water or an organic liquid in which the toxicant is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate according to the invention with water, also lie within the scope of the present invention.

The compositions of the invention may also contain other ingredients, for example, other compounds possessing pesticidal, herbicidal or fungicidal properties, or attractants, such as pheromones, attractive food ingredients, and the like, for use in baits and trap formulations.

These compositions are applied in sufficient amount to supply the effective dosage of toxicant at the locus to be protected. This dosage is dependent upon many factors, including the carrier employed, the method and conditions of application, whether the formulation is present at the locus in the form of an aerosol, or as a film, or as discrete particles, the thickness of film or size of particles, the insect species to be controlled and the like, proper consideration and resolution of these factors to provide the necessary dosage of active material at the locus being within the skill of those versed in the art. In general, however, the effective dosage of toxicants of this invention at the locus to be protected — i.e. the dosage to which the insect contacts — is of the order of 0.001% to 0.5% based on the total weight of the formulation, though under some circumstances the effective concentration will be as little as 0.0001% or as much as 2%, on the same basis.

I claim as my invention:

1. A compound of the formula:

$$\begin{array}{c} \text{(ring with S, N, and O)} \\ S \quad N-\overset{\overset{O}{\|}}{C}-X \\ \underset{Y-\overset{\|}{C}-\overset{\|}{C}-NO_2}{\overset{O}{\|}} \end{array}$$

wherein X and Y each is R, R—O— or R—S—, R containing up to 30 carbon atoms and being alkyl, alkenyl, alkynyl, cycloalkyl, cycloalkylalkyl, haloalkyl, haloalkenyl, mono- and poly(alkoxy)alkyl, alkylthioalkyl, alkylsulfinylalkyl, alkylsulfonylalkyl; phenyl, or phenalkyl, or any of these substituted on the ring by one to two of one or more of halogen, nitro, cyano, alkyl, phenyl, alkoxy or phenoxy; is aminoalkyl, $-(CH_2)_m-NR^1R^2$, wherein $m$ is one or two, $R^1$ and $R^2$ is alkyl, alkenyl, cycloalkyl, phenyl or phenalkyl; or is $-(CH_2)_n-R^5$, wherein $n$ is zero, one or two, and $R^5$ is heterocyclic moiety selected from furanyl, tetrahydrofuranyl, dioxolanyl, thienyl, thiopyranyl, pyridinyl, pyrrolidinyl, morpholinyl and their -methyl and -ethyl counterparts.

* * * * *

UNITED STATES PATENT AND TRADEMARK OFFICE
CERTIFICATE OF CORRECTION

PATENT NO. : 4,022,775
DATED : May 10, 1977
INVENTOR(S) : STEVEN A. ROMAN and JAMES E. POWELL It is certified that error appears in the above-identified patent and that said Letters Patent are hereby corrected as shown below:

Column 1, line 37, place a period after "morpholinyl", and cancel "and their -methyl and -ethyl counterparts.".

Claim 1, last line, place a period after "morpholinyl", and cancel "and their -methyl and -ethyl counterparts.".

Signed and Sealed this

Eleventh Day of October 1977

[SEAL]

Attest:

RUTH C. MASON
Attesting Officer

LUTRELLE F. PARKER
Acting Commissioner of Patents and Trademarks